(12) United States Patent
Dorn (10) Patent No.: US 9,833,349 B2
(45) Date of Patent: Dec. 5, 2017

(54) METHOD OF LOADING A STENT INTO A SHEATH

(75) Inventor: Juergen Dorn, Neulussheim (DE)

(73) Assignee: C. R. Bard, Inc., Tempe, AZ (US)

( * ) Notice: Subject to any disclaimer, the term of this patent is extended or adjusted under 35 U.S.C. 154(b) by 1716 days.

(21) Appl. No.: 12/545,409

(22) Filed: Aug. 21, 2009

(65) Prior Publication Data

US 2010/0049297 A1  Feb. 25, 2010

Related U.S. Application Data

(60) Provisional application No. 61/090,772, filed on Aug. 21, 2008.

(30) Foreign Application Priority Data

Aug. 21, 2008 (GB) .................................. 0815339.7

(51) Int. Cl.
| | | |
|---|---|---|
| *A61F 2/06* | (2013.01) | |
| *A61F 2/97* | (2013.01) | |
| *A61F 2/966* | (2013.01) | |
| *A61F 2/95* | (2013.01) | |

(52) U.S. Cl.
CPC ............... *A61F 2/97* (2013.01); *A61F 2/966* (2013.01); *A61F 2002/9511* (2013.01); *A61F 2002/9522* (2013.01)

(58) Field of Classification Search
CPC .... A61F 2/95; A61F 2002/9522; A61F 2/958; A61F 2002/9583; A61F 2/962; A61F 2002/9665; A61F 2/97; A61F 2/966; A61F 2/0095; A61F 2/844; A61F 2002/011; A61F 2002/9511; A61F 2002/9528;

(Continued)

(56) References Cited

U.S. PATENT DOCUMENTS

| | | | | |
|---|---|---|---|---|
| 3,953,566 A | * | 4/1976 | Gore | ............................. 264/505 |
| 3,962,153 A | * | 6/1976 | Gore | ............................. 521/79 |
| 4,187,390 A | * | 2/1980 | Gore | ......................... 174/102 R |

(Continued)

FOREIGN PATENT DOCUMENTS

| | | | | |
|---|---|---|---|---|
| DE | 10339628 A1 | * | 3/2005 | ............... A61F 2/82 |
| DE | 10339628 A1 | | 3/2005 | |

(Continued)

OTHER PUBLICATIONS

Translation of DE10339628.*

(Continued)

*Primary Examiner* — Anh Dang
*Assistant Examiner* — Erin Colello (57) ABSTRACT

A method of loading a self-expanding stent into a delivery sheath configured to retain the stent in a radially compressed pre-deployment configuration, including the steps of radially compressing the stent from a relaxed outside diameter d0 to a compressed outside diameter d1, providing a loading sheath with an inner diameter d2, where d0>d2>d1, translating the stent relative to the sheath, whereby the stent is accommodated within the lumen of the loading sheath, providing a delivery sheath with an inner diameter d3, where d0>d3>d2, advancing the loading sheath, containing the stent, into the lumen of the delivery sheath, and deploying the stent into the lumen of the delivery sheath.

18 Claims, 7 Drawing Sheets

(58) Field of Classification Search
CPC .. A61F 2002/9534; A61B 2017/00336; A61M 2025/1081
USPC ...... 623/1.11, 1.12, 1.2, 1.23; 264/479, 539, 264/540, 197, 198, 288.4, 208, 209.5, 264/210.1, 210.7, 291, 181
See application file for complete search history.

(56) References Cited

U.S. PATENT DOCUMENTS

| | | | |
|---|---|---|---|
| 4,636,162 A * | 1/1987 | Pavy et al. .................. 425/290 |
| 4,732,152 A | 3/1988 | Wallsten et al. |
| 5,015,231 A * | 5/1991 | Keith ................ A61M 25/1038 604/103 |
| 5,026,377 A * | 6/1991 | Burton ...................... A61F 2/82 606/108 |
| 5,087,394 A * | 2/1992 | Keith .......................... 264/470 |
| 5,217,482 A | 6/1993 | Keith |
| 5,324,261 A * | 6/1994 | Amundson et al. ...... 604/103.02 |
| 5,415,664 A * | 5/1995 | Pinchuk ................... A61F 2/95 604/523 |
| 5,453,090 A | 9/1995 | Martinez et al. |
| 5,573,520 A | 11/1996 | Schwartz et al. |
| 5,626,605 A * | 5/1997 | Irie ........................... A61F 2/01 606/200 |
| 5,647,857 A * | 7/1997 | Anderson et al. ............ 604/264 |
| 5,662,703 A | 9/1997 | Yurek et al. |
| 5,690,644 A | 11/1997 | Yurek et al. |
| 5,709,703 A | 1/1998 | Lukic et al. |
| 5,718,861 A * | 2/1998 | Andrews et al. ............. 264/235 |
| 5,755,769 A | 5/1998 | Richard et al. |
| 5,765,682 A * | 6/1998 | Bley et al. .................. 206/363 |
| 5,807,520 A | 9/1998 | Wang et al. |
| 5,823,995 A | 10/1998 | Fitzmaurice et al. |
| 5,824,041 A | 10/1998 | Lenker et al. |
| 5,833,694 A | 11/1998 | Poncet |
| 5,843,027 A | 12/1998 | Stone et al. |
| 5,925,061 A | 7/1999 | Ogi et al. |
| 5,968,069 A | 10/1999 | Dusbabek et al. |
| 5,992,000 A * | 11/1999 | Humphrey et al. ............ 29/516 |
| 6,027,510 A | 2/2000 | Alt |
| 6,033,413 A * | 3/2000 | Mikus ................... A61F 2/0009 604/102.01 |
| 6,063,092 A | 5/2000 | Shin |
| 6,126,685 A | 10/2000 | Lenker et al. |
| 6,149,681 A | 11/2000 | Houser et al. |
| 6,168,748 B1 * | 1/2001 | Wang et al. .................. 264/520 |
| 6,224,803 B1 * | 5/2001 | Tiernan ....................... 264/166 |
| 6,254,609 B1 * | 7/2001 | Vrba ......................... A61F 2/01 606/108 |
| 6,254,628 B1 | 7/2001 | Wallace et al. |
| 6,309,383 B1 * | 10/2001 | Campbell et al. ................. 606/1 |
| 6,368,344 B1 | 4/2002 | Fitz |
| 6,425,898 B1 | 7/2002 | Wilson et al. |
| 6,447,540 B1 * | 9/2002 | Fontaine et al. ............. 623/1.12 |
| 6,613,067 B1 * | 9/2003 | Johnson ........................ 606/194 |
| 6,613,075 B1 | 9/2003 | Healy et al. |
| 6,629,992 B2 * | 10/2003 | Bigus et al. ................. 623/1.12 |
| 6,645,238 B2 | 11/2003 | Smith |
| 6,702,843 B1 * | 3/2004 | Brown et al. ................. 623/1.11 |
| 6,805,703 B2 * | 10/2004 | McMorrow .................. 623/1.11 |
| 6,830,575 B2 * | 12/2004 | Stenzel ...................... A61F 2/95 606/108 |
| 6,833,002 B2 * | 12/2004 | Stack et al. .................. 623/1.11 |
| 6,837,870 B2 | 1/2005 | Dunchamp |
| 6,841,029 B2 | 1/2005 | Lim |
| 6,902,575 B2 * | 6/2005 | Laakso ...................... A61F 2/95 623/1.11 |
| 6,946,092 B1 * | 9/2005 | Bertolino et al. .............. 264/512 |
| 7,604,668 B2 | 10/2009 | Farnsworth |
| 7,815,669 B2 | 10/2010 | Matsuoka et al. |
| 7,993,350 B2 * | 8/2011 | Ventura ............. A61B 17/3439 606/108 |
| 8,308,789 B2 * | 11/2012 | Armstrong ....... A61B 17/12022 623/1.11 |
| 8,359,721 B2 * | 1/2013 | Melsheimer ............. A61F 2/95 29/235 |
| 8,414,528 B2 * | 4/2013 | Liu ....................... A61F 2/0095 604/103.05 |
| 8,535,368 B2 * | 9/2013 | Headley, Jr. ............. A61F 2/95 623/1.12 |
| 8,568,467 B2 | 10/2013 | Dorn et al. |
| 8,852,257 B2 * | 10/2014 | Liu ......................... A61F 2/958 623/1.11 |
| 9,119,741 B2 * | 9/2015 | Liu ....................... A61F 2/0095 |
| 9,125,761 B2 * | 9/2015 | Wood ....................... A61F 2/95 |
| 2001/0001128 A1 * | 5/2001 | Holman ................. A61F 2/0095 623/1.11 |
| 2001/0011180 A1 | 8/2001 | Fitzmaurice et al. |
| 2001/0027323 A1 | 10/2001 | Sullivan et al. |
| 2002/0016597 A1 | 2/2002 | Dwyer et al. |
| 2002/0055767 A1 * | 5/2002 | Forde ........................ A61F 2/01 623/1.11 |
| 2002/0099431 A1 * | 7/2002 | Armstrong et al. ......... 623/1.11 |
| 2002/0180107 A1 * | 12/2002 | Jackson et al. ............. 264/288.4 |
| 2003/0083730 A1 * | 5/2003 | Stinson ..................... A61F 2/95 623/1.11 |
| 2003/0109886 A1 | 6/2003 | Keegan et al. |
| 2003/0114912 A1 | 6/2003 | Sequin et al. |
| 2003/0125709 A1 | 7/2003 | Eidenschink |
| 2003/0125791 A1 | 7/2003 | Sequin et al. |
| 2003/0139801 A1 | 7/2003 | Sirhan et al. |
| 2003/0163193 A1 | 8/2003 | Widenhouse |
| 2003/0204235 A1 * | 10/2003 | Edens et al. .................. 623/1.5 |
| 2004/0064130 A1 | 4/2004 | Carter |
| 2004/0143272 A1 * | 7/2004 | Cully et al. .................. 606/108 |
| 2004/0143286 A1 | 7/2004 | Johnson et al. |
| 2004/0143315 A1 * | 7/2004 | Bruun ........................ A61F 2/95 623/1.11 |
| 2004/0148007 A1 * | 7/2004 | Jackson .................... A61F 2/95 623/1.12 |
| 2004/0199239 A1 * | 10/2004 | Austin et al. ................. 623/1.11 |
| 2004/0267346 A1 | 12/2004 | Shelso |
| 2005/0004555 A1 | 1/2005 | Pursley |
| 2005/0049667 A1 | 3/2005 | Arbefeuille et al. |
| 2005/0113902 A1 | 5/2005 | Geiser et al. |
| 2005/0240254 A1 | 10/2005 | Austin |
| 2006/0015171 A1 * | 1/2006 | Armstrong ....... A61B 17/12022 623/1.12 |
| 2006/0030923 A1 | 2/2006 | Gunderson |
| 2006/0089627 A1 | 4/2006 | Burnett et al. |
| 2006/0100687 A1 | 5/2006 | Fahey et al. |
| 2006/0142838 A1 * | 6/2006 | Molaei et al. ................ 623/1.12 |
| 2006/0212105 A1 | 9/2006 | Dorn et al. |
| 2006/0247661 A1 | 11/2006 | Richards et al. |
| 2006/0259124 A1 | 11/2006 | Matsuoka et al. |
| 2007/0050017 A1 | 3/2007 | Sims et al. |
| 2007/0055338 A1 | 3/2007 | Dorn |
| 2007/0074805 A1 | 4/2007 | Leeflang et al. |
| 2007/0270932 A1 * | 11/2007 | Headley ..................... A61F 2/95 623/1.11 |
| 2008/0118546 A1 | 5/2008 | Thatcher et al. |
| 2008/0243224 A1 | 10/2008 | Wallace et al. |
| 2009/0125093 A1 | 5/2009 | Hansen |
| 2009/0204196 A1 | 8/2009 | Weber |
| 2009/0254169 A1 | 10/2009 | Spenser et al. |
| 2009/0312828 A1 | 12/2009 | Vrba |
| 2009/0312831 A1 | 12/2009 | Dorn |
| 2010/0049297 A1 | 2/2010 | Dorn |
| 2010/0168835 A1 | 7/2010 | Dorn |
| 2010/0249907 A1 | 9/2010 | Dorn et al. |
| 2011/0060397 A1 | 3/2011 | Dorn |
| 2011/0137396 A1 | 6/2011 | Dorn et al. |
| 2011/0137400 A1 | 6/2011 | Dorn et al. |
| 2011/0137401 A1 | 6/2011 | Dorn et al. |
| 2011/0137402 A1 | 6/2011 | Dorn et al. |
| 2012/0059448 A1 | 3/2012 | Parker et al. |
| 2012/0143303 A1 | 6/2012 | Dorn et al. |
| 2012/0302955 A1 * | 11/2012 | Liu ....................... A61F 2/0095 604/103.05 |
| 2012/0324696 A1 * | 12/2012 | Liu ......................... A61F 2/958 29/428 |

(56) References Cited

U.S. PATENT DOCUMENTS

| | | | | |
|---|---|---|---|---|
| 2013/0218256 | A1* | 8/2013 | Liu | A61F 2/0095 623/1.12 |
| 2014/0379064 | A1* | 12/2014 | Pacetti | A61L 31/048 623/1.11 |
| 2014/0379065 | A1* | 12/2014 | Johnson | A61F 2/958 623/1.11 |
| 2015/0088241 | A1* | 3/2015 | Liu | A61F 2/958 623/1.11 |

FOREIGN PATENT DOCUMENTS

| | | |
|---|---|---|
| EP | 0732087 A1 | 9/1996 |
| EP | 0941713 A1 | 9/1999 |
| EP | 1062966 A1 | 12/2000 |
| EP | 0732087 B1 | 6/2003 |
| EP | 1679095 A1 * | 7/2006 |
| FR | 2688688 A1 | 9/1993 |
| JP | S59-51863 A | 3/1984 |
| JP | H09-512194 A | 12/1997 |
| JP | 2000-116788 A | 4/2000 |
| JP | 2001-9037 | 1/2001 |
| JP | 2001-299926 A | 10/2001 |
| JP | 2006-515786 A | 6/2006 |
| WO | 8603398 A1 | 6/1986 |
| WO | 9317636 A1 | 9/1993 |
| WO | 9415549 A1 | 7/1994 |
| WO | 9530385 A1 | 11/1995 |
| WO | 9632078 A1 | 10/1996 |
| WO | 9820812 A1 | 5/1998 |
| WO | WO-0018329 A1 | 4/2000 |
| WO | 0108599 A1 | 2/2001 |
| WO | 02/38084 A2 | 5/2002 |
| WO | 03002019 A2 | 1/2003 |
| WO | 03002034 A2 | 1/2003 |
| WO | 2004062458 A2 | 7/2004 |
| WO | 2004066809 A2 | 8/2004 |
| WO | 2004096091 A1 | 11/2004 |
| WO | 2005072650 A1 | 8/2005 |
| WO | 2006019626 A2 | 2/2006 |
| WO | 2006020028 A1 | 2/2006 |
| WO | WO-2006071245 A1 | 7/2006 |
| WO | WO 2006071245 A1 * | 7/2006 |
| WO | WO-2006086709 A1 | 8/2006 |
| WO | 2006096229 A1 | 9/2006 |
| WO | 2006130326 A2 | 12/2006 |
| WO | 2007103666 A2 | 9/2007 |
| WO | 2009050265 A1 | 4/2009 |
| WO | 2009135934 A1 | 11/2009 |
| WO | 2010076052 A1 | 7/2010 |
| WO | 2010076057 A1 | 7/2010 |
| WO | 2010115925 A1 | 10/2010 |
| WO | 2011067277 A1 | 6/2011 |
| WO | 2011067280 A1 | 6/2011 |
| WO | 2012072729 A1 | 6/2012 |

OTHER PUBLICATIONS

Translation of EP0941713.*
English Translation of DE10339628.*
Nov. 5, 2009 International Search Report in International Application No. PCT/EP2009/060827 filed on Aug. 21, 2009.
Nov. 5, 2009 Written Opinion of the ISA in international application No. PCT/EP2009/060827 filed on Aug. 21, 2009.
PCT/EP2009/055592 filed May 8, 2009 International Preliminary Report on Patentability dated Nov. 9, 2010.
PCT/EP2009/055592 filed May 8, 2009 Written Opinion dated Aug. 3, 2009.
PCT/EP2009/055592 filed May 8, 2009 Search Report dated Aug. 3, 2009.
PCT/EP2009/060827 filed Aug. 21, 2009 Preliminary Report on Patentability dated Oct. 19, 2010.
Dec. 22, 2008 European Search Report in European application No. 0815339.7.
U.S. Appl. No. 12/991,112, filed Nov. 4, 2010 Non-Final Office Action dated Apr. 3, 2012.
EP 12164925.5 filed Jul. 6, 2011 Extended European Search Report dated Jul. 26, 2012.
PCT/EP2008/064036 filed Oct. 17, 2008 International Preliminary Examination Report dated Apr. 20, 2010.
PCT/EP2008/064036 filed Oct. 17, 2008 Search Report dated Jan. 22, 2009.
PCT/EP2008/064036 filed Oct. 17, 2008 Written Opinion dated Jan. 22, 2009.
PCT/EP2009/064057 filed Oct. 26, 2009 International Preliminary Report on Patentability dated Jun. 6, 2011.
PCT/EP2009/064057 filed Oct. 26, 2009 International Search Report dated May 17, 2010.
PCT/EP2009/064057 filed Oct. 26, 2009 Written Opinion dated May 17, 2010.
PCT/EP2010/068620 filed Dec. 1, 2010 International Preliminary Report on Patentability dated Aug. 5, 2011.
PCT/EP2010/068620 filed Dec. 1, 2010 International Search Report dated Apr. 21, 2011.
PCT/EP2010/068620 filed Dec. 1, 2010 Written Opinion dated Apr. 21, 2011.
PCT/EP2010/068627 filed Dec. 1, 2010 International Preliminary Report on Patentability dated Jul. 20, 2011.
PCT/EP2010/068627 filed Dec. 1, 2010 International Search Report dated Apr. 21, 2011.
PCT/EP2010/068627 filed Dec. 1, 2010 Written Opinion dated Apr. 21, 2011.
PCT/EP2011/071489 filed Dec. 1, 2011 International Search Report dated Mar. 6, 2012.
U.S. Appl. No. 12/650,863, filed Dec. 31, 2009 Advisory Action dated Dec. 31, 2012.
U.S. Appl. No. 12/650,863, filed Dec. 31, 2009 Final Office Action dated Oct. 11, 2012.
U.S. Appl. No. 12/650,863, filed Dec. 31, 2009 Non-Final Office Action dated Jun. 8, 2012.
U.S. Appl. No. 12/738,568, filed Apr. 16, 2010 Advisory Action dated Jun. 10, 2013.
U.S. Appl. No. 12/738,568, filed Apr. 16, 2010 Final Office Action dated Mar. 29, 2013.
U.S. Appl. No. 12/738,568, filed Apr. 16, 2010 Non-Final Office Action dated Nov. 2, 2012.
U.S. Appl. No. 12/958,089, filed Dec. 1, 2010 Non-Final Office Action dated Mar. 14, 2013.
U.S. Appl. No. 12/958,123, filed Dec. 1, 2010 Non-Final Office Action dated Mar. 25, 2013.
U.S. Appl. No. 12/958,184, filed Dec. 1, 2010 Non-Final Office Action dated Mar. 14, 2013.
U.S. Appl. No. 12/958,220, filed Dec. 1, 2010 Non-Final Office Action dated Mar. 15, 2013.
U.S. Appl. No. 12/991,112, filed Nov. 4, 2010 Final Office Action dated May 9, 2013.
U.S. Appl. No. 13/309,420, filed Dec. 1, 2011 Non-Final Office Action dated Apr. 15, 2013.
JP 2011-523429 Office Action dated Jan. 6, 2014.
JP 2011-523429 Office Action dated Jul. 17, 2013.
U.S. Appl. No. 12/958,089, filed Dec. 1, 2010 Advisory Action dated Oct. 28, 2013.
U.S. Appl. No. 12/958,089, filed Dec. 1, 2010 Final Office Action dated Aug. 15, 2013.
U.S. Appl. No. 12/958,123, filed Dec. 1, 2010 Advisory Action dated Oct. 17, 2013.
U.S. Appl. No. 12/958,184, filed Dec. 1, 2010 Final Office Action dated Aug. 14, 2013.
U.S. Appl. No. 12/958,220, filed Dec. 1, 2010 Final Office Action dated Aug. 13, 2013.
U.S. Appl. No. 12/991,112, filed Nov. 4, 2010 Non-Final Office Action dated Mar. 21, 2014.
U.S. Appl. No. 13/309,420, filed Dec. 1, 2011 Advisory Action dated Feb. 13, 2014.
U.S. Appl. No. 13/309,420, filed Dec. 1, 2011 Final Office Action dated Nov. 8, 2013.

(56) References Cited

OTHER PUBLICATIONS

PCT/EP2009/060827 filed Aug. 21, 2009 Search Report dated Nov. 16, 2009.
U.S. Appl. No. 12/650,863, filed Dec. 31, 2009 Non-Final Office Action dated Jan. 7, 2015.
U.S. Appl. No. 12/650,863, filed Dec. 31, 2009 Final Office Action dated Jul. 28, 2015.
U.S. Appl. No. 12/958,089, filed Dec. 1, 2010 Final Office Action dated Nov. 19, 2014.
U.S. Appl. No. 12/958,089, filed Dec. 1, 2010 Non-Final Office Action dated Jun. 20, 2014.
U.S. Appl. No. 12/958,089, filed Dec. 1, 2010 Non-Final Office Action dated Jul. 2, 2015.
U.S. Appl. No. 12/958,123, filed Dec. 1, 2010 Advisory Action dated Feb. 10, 2015.
U.S. Appl. No. 12/958,123, filed Dec. 1, 2010 Final Office Action dated Nov. 19, 2014.
U.S. Appl. No. 12/958,123, filed Dec. 1, 2010 Non-Final Office Action dated Jun. 11, 2014.
U.S. Appl. No. 12/958,123, filed Dec. 1, 2010 Non-Final Office Action dated Aug. 19, 2015.
U.S. Appl. No. 12/958,184, filed Dec. 1, 2010 Advisory Action dated Nov. 5, 2013.
U.S. Appl. No. 12/958,184, filed Dec. 1, 2010 Final Office Action dated Feb. 10, 2015.
U.S. Appl. No. 12/958,184, filed Dec. 1, 2010 Non-Final Office Action dated Aug. 5, 2014.
U.S. Appl. No. 12/958,184, filed Dec. 1, 2010 Advisory Action dated May 18, 2015.
U.S. Appl. No. 12/958,184, filed Dec. 1, 2010 Non-Final Office Action date Aug. 10, 2015.
U.S. Appl. No. 12/958,220, filed Dec. 1, 2010 Advisory Action dated Nov. 5, 2013.
U.S. Appl. No. 12/958,220, filed Dec. 1, 2010 Final Office Action dated Oct. 23, 2014.
U.S. Appl. No. 12/958,220, filed Dec. 1, 2010 Non-Final Office Action dated Apr. 9, 2014.
U.S. Appl. No. 12/958,220, filed Dec. 1, 2010 Non-Final Office Action dated Jul. 21, 2015.
U.S. Appl. No. 12/991,112, filed Nov. 4, 2010 Final Office Action dated Sep. 11, 2014.
U.S. Appl. No. 12/991,112, filed Nov. 4, 2010 Advisory Action dated Dec. 23, 2014.
U.S. Appl. No. 13/309,420, filed Dec. 1, 2011 Final Office Action dated Feb. 24, 2015.
U.S. Appl. No. 13/309,420, filed Dec. 1, 2011 Non-Final Office Action dated Aug. 19, 2014.
U.S. Appl. No. 13/309,420, filed Dec. 1, 2011 Notice of Allowance dated Jul. 9, 2015.

* cited by examiner

Fig. 3

METHOD OF LOADING A STENT INTO A SHEATH

PRIORITY

This application claims the priority benefit of U.S. Provisional Application No. 61/090,772, filed Aug. 21, 2008, and U.K. Patent Application No. GB 0815339.7, filed Aug. 21, 2008. This application expressly incorporates by reference the entirety of each of the above-mentioned applications as if fully set forth herein.

FIELD OF THE INVENTION

This invention relates to a method of loading a self-expanding stent into a delivery sheath that is part of a catheter for transluminal delivery of the stent to a stenting location in the body of a patient, with the stent being deployed at that location by removal from the stent of the constraint on its radial expansion that is provided up to that point by the sheath.

Stent designers are succeeding in creating ever more sophisticated stents and stent grafts, for location in ever more sites in the body. There is consequently pressure on designers of stent delivery systems to come up with designs for catheters that will reach ever more demanding requirements to convey such stents to the desired locations in the body.

The usual way to express a stent diameter is in units of "French". One French is one third of a millimetre. Thus, a stent delivery system with a passing diameter of "6 French" has an outside diameter of 2 mm. For a manufacturer of stents and stent delivery systems, a reduction of diameter from, say, 6 French to 5 French is a powerful technical advantage, and a great challenge for designers of stents and stent delivery systems. Measures that are capable of delivering even the tiniest reduction of the passing diameter of a stent delivery catheter might still be of considerable interest to such designers, provided the catheter is still as flexible, pushable and capable of reliable operations as a fatter catheter.

BACKGROUND

Catheter delivery systems are commonly used to introduce self-expanding endoprostheses in human or animal bodies and to advance them to the clogged or narrowed area. In the delivery system, the elongate endoprosthesis is held in a radially compressed state by a surrounding sheath to facilitate a smooth delivery. When the endoprosthesis has been placed in the destined area, it is expanded by withdrawing or opening up the sheath.

A catheter delivery system where the endoprosthesis is expanded by cutting open the sheath is disclosed in FR 2688688, which is incorporated by reference into this application. In this system, three cutting wires are arranged equidistantly around the periphery of the endoprosthesis. Each wire runs from a proximal end of the catheter to a distal end, with the wire placed between the radially compressed endoprosthesis and the sheath in the region where the endoprosthesis is received, leaves the sheath at its distal end and runs back to the proximal catheter end along the outside of the sheath, so as to form a loop around the sheath wall. Both parts of the wires, in- and outside the sheath, are guided parallel to one another and the overall six proximal wire ends are attached to a handle at the proximal end of the catheter. The sheath is opened by pulling the handle so that the distal ends of the three wire loops move proximally and cut through the wall of the sheath.

A catheter delivery system that uses only one cutting wire is disclosed in WO-A-01/08599, which is incorporated by reference into this application. The wire consists of an inner pull element, running within the sheath, an outer pull element, running outside the sheath, and a separating element, located between the distal ends of the two pull elements at the distal end of the sheath. In order to expand the endoprosthesis, both pull elements are simultaneously pulled in a proximal direction, so that the separating element moves along the endoprosthesis towards the proximal catheter end and cuts through the sheath wall. Also belonging to the state of the art is WO2004/066809, which is incorporated by reference into this application, and which suggests the use of a deployment line that is integral with a pull back sheath, to release an endoluminal device from inside the sheath.

In known catheter delivery systems that use a cutting mechanism to open up the sheath, the cut open sheath is trapped between the expanded endoprosthesis and the wall of the vessel, once the expansion process is finished. To remove the sheath from the patient's body, it has to be pulled out from its proximal end. For the case of relatively large endoprostheses, such as oesophagus stents, where sheaths with thick walls can be used, this procedure is normally uncomplicated. However, problems arise when small-sized endoprostheses are required, for example to widen narrow blood vessels. In this case, the profile of the distal catheter end, comprising the endoprosthesis to be deployed, has to be strongly reduced, in order to facilitate accurate placement of the endoprosthesis and thus sheaths with thin walls have to be used. When such a thin-walled, cut open sheath is removed from the patient's body by pulling from its proximal end, the friction generated by the abluminal surface of the expanded endoprosthesis and the luminal surface of the vessel may cause either the sheath to tear, inhibiting its complete removal, or the endoprosthesis to move proximally with the sheath being pulled away from the axial position in the bodily lumen where it ought to be. Similar friction problems may arise even in traditional deployment methods, where an unslitted sheath is withdrawn from the endoprosthesis in the expansion process. When pulled from the proximal end, a thin-walled sheath may stretch along the direction of the pull, leading to a decrease of its radial diameter. This increases the friction caused between sheath and endoprosthesis, requiring a larger pulling force to move the sheath, similar to the known concept of the "Chinese finger trap". Eventually, the sheath may tear or the endoprosthesis may move away from the desired position.

While one way to release a stent from the constraint of a sheath is to run a slitter down the length of the sheath that surrounds the stent (see, for example, WO 01/08599, WO 93/17636 and WO 98/20812, each of which is incorporated by reference into this application), a far more commonly used method is to pull the sheath proximally, relative to the stent, to release the stent progressively, starting at its distal end. See, for example, U.S. Pat. No. 5,833,694 Poncet, which is incorporated by reference into this application. However, pulling on the sheath from its proximal end will impose tensile stresses on the sheath material, in the length direction of the sheath. The sheath must therefore be physically strong enough, not only to resist the radially outward spring force that is coming from the self-expanding stent constrained within the sheath, but also the stresses to which the sheath is subject during the time that it is being pulled proximally, to release the stent. A force that tends to stretch a tube will also tend to reduce the diameter of that tube. A simple example is the toy called the "Chinese finger" that is in the form of a braided tube. The child slips it over his finger and then pulls the free end of the tube, causing the braiding to neck down, and grip tightly the finger within the lumen of the braided tube. Intuitively, one can appreciate that pulling on a sheath from the proximal end, when there is a self-expanding stent inside the lumen of the sheath, is a situation fraught with the possibility of unwanted additional, friction-generated loads that might be an impediment to smooth release of the stent.

One can appreciate that the wall thickness of the sheath makes a contribution to the totality of the passing profile of the stent delivery system, at least at the distal end of the catheter delivery system, in the "capsule" that contains the stent to be delivered by that system, for any such capsule is liable to be that portion of the length of the catheter that exhibits the greatest passing diameter. It is normally possible to devise a catheter delivery system in which the length of the catheter, the shaft, between the proximal end of the catheter held in the hand of the operator, and the distal end that exhibits the capsule containing the stent, will be of smaller passing diameter. Thus, designers are interested to reduce the wall thickness of the sheath surrounding the self-expanding stent, to the extent that is possible, consistent with safe operation of the system. It is of course intolerable for the sheath component to fail during deployment of the stent. The sheath component must be robust enough to withstand less than optimal handling of the stent delivery system, by medical practitioners, during placement of the stent.

It is an object of the present invention to advance stent delivery system design to achieve a smaller passing profile, consistent with simplicity of design and reliability of operation.

SUMMARY

In accordance with one aspect of the present invention there is provided a method of loading a self-expanding stent into a delivery sheath configured to retain the stent in a radially compressed pre-deployment configuration, comprising the steps of:
i) radially compressing the stent from a relaxed outside diameter d0 to a compressed outside diameter d1;
ii) providing a loading sheath with an inner diameter d2, where d0>d2>d1;
iii) translating the stent relative to the sheath, whereby the stent is accommodated within the lumen of the loading sheath;
iv) providing a delivery sheath with an inner diameter d3, where d0>d3>d2;
v) advancing the loading sheath, containing the stent, into the lumen of the delivery sheath; and
vi) deploying the stent into the lumen of the delivery sheath.

In accordance with another aspect of the present invention, there is provided apparatus for installing a self-expanding stent in a sheath of a stent delivery catheter, the apparatus comprising a loading sheath with a lumen for containing the self-expanding stent, the apparatus deploying the stent into the delivery sheath by advancing into the lumen of the delivery sheath the loading sheath containing the stent, and then withdrawing from the lumen of the delivery sheath the loading sheath but not the stent.

According to a further aspect of the present invention there is provided a self-expanding stent (or stent graft) within the lumen of a delivery sheath of a stent delivery system, the delivery sheath being formed of polymeric material that has been cold drawn with the stent in situ, within the lumen of the sheath.

In a preferred embodiment of the method of the invention, the step of deploying the stent into the lumen of the delivery sheath is effected by withdrawing the loading sheath while restraining the stent from relative axial movement out of the lumen of the delivery sheath.

In a preferred embodiment of the method of the invention, the delivery sheath is subject to a lengthwise strain, after the stent has been installed in the lumen of the sheath, to draw down the inner diameter of the delivery sheath to a diameter d4, which is less than diameter d3. The diameter d4 may be freely chosen, and may for example be less than d2, d1 or potentially even d0, depending on the degree of compression which is required to be achieved. In general, a balance is selected between minimising the diameter of the sheathed stent and permitting the stent to be easily deployed in the body.

In one preferred embodiment, the delivery sheath is one which can be parted along a line extending axially the full length of the stent, to allow the stent to push the material of the longitudinally parted sheath of the way, during the radial expansion of the stent that occurs as the stent deploys into a bodily lumen. Conveniently, the sheath is made of polyethyleneterephthalate (PET) and typically has a wall thickness of the order of 20 µm, presently preferably 30 µm prior to any drawing down of the diameter after placement of the stent in the lumen of the sheath.

It may be useful to design into the sheath a specific zone for initiation of the cold drawing strain, so that such strain spreads outwardly, progressively, along the length of the sheath, from the strain initiation zone, upon imposition on the sheath of the longitudinal stress needed to initiate the strain. Generally, it will be convenient to locate any such strain initiation zone somewhere between the opposite ends of the stent, such as midway along the length of the stent. The form of any such strain initiation zone could be a portion of the sheath that exhibits a reduced wall thickness.

Medical practitioners are seeking ever longer and more flexible stents. Such stents are correspondingly more problematic to handle, in such a way that no portion of the stent matrix is ever subject to a level of stress that prejudices the fatigue performance of the stent. Whereas short and robust stents tolerate being pushed from one end, long and flexible delicate stent designs are vulnerable to over-stressing, if not supported along their full length during loading into a sheath and during deployment out of that sheath. One way to provide support for a stent graft along the full length of the lumen of that graft can be found in the disclosure of Applicant's WO 2004/096091, which is incorporated by reference in its entirety into this application. Thus, for loading a stent or stent graft into the loading sheath of the present invention, it will generally be desirable to employ a tool that extends along the lumen of the stent and supports the stent matrix from within that lumen. Once the stent has been installed in the delivery sheath, designers have the option of leaving the tool in place, within the lumen of the stent, for making a contribution to the construction and operation of the delivery system for the stent or, in the alternative, removing the tool from the lumen of the stent, once the stent has been installed in the delivery sheath, and using for stent support during deployment of the stent some other component within the construction of the delivery system. Thus, an optional feature of the method of the present invention is the step of introducing into the lumen of the stent, as part of the process of installing the stent in the delivery sheath, a component of the delivery system that will deliver the stent to the stenting site within the body.

As for strategies for releasing the stent from the sheath, when the stent is deployed in the body at a stenting site, a number of techniques are described in an enabling manner hereinbelow.

As to the drawing down step, it is to be remembered that the sheath is of remarkably small wall thickness and so amenable to being cold-drawn in a simple manual operation in which the sheath is gripped in the hands of a skilled person. The left and right hands can simply be pulled apart from each other, simply to stretch the sheath in the portion of its length surrounding the stent. However, such procedures are not ideally suited to meet rigorous quality control procedures. It is therefore envisaged that the manually-achieved cold drawing step will, in real production, be replaced by a rigorously specified mechanical step so that the stretching process is performed always in the same way, for every delivery system produced. One envisages machine components that constitute first and second sheath grippers, one at each end of the sheath, beyond the respective end of the stent within the sheath, such grippers likely gripping the sheath all around the circumference of the sheath, probably with a high enough friction grip to hold the sheath ends securely, possibly with grip surfaces of silicone rubber material, with the first and second sheath grippers moving apart from each other in a controlled fashion, with sensors to provide control engineering feedback so that the sheath is always cold-drawn in the same manner.

Sheath delivery systems with a distal end capsule having an outside diameter of 6 French, or even less, are well within the contemplation of the inventors of the present invention. For manufacturing efficiency, a single size of loading sheath, for example diameter 8 French, can be used for loading a variety of sizes of stent, from e.g. a deployed diameter of 4 mm to 10 mm.

BRIEF DESCRIPTION OF THE DRAWINGS

For a better understanding of the present invention, and to show more clearly how the same may be carried into effect, reference will now be made, by way of example, to the accompanying drawings, in which.

DETAILED DESCRIPTION

Figure 1:
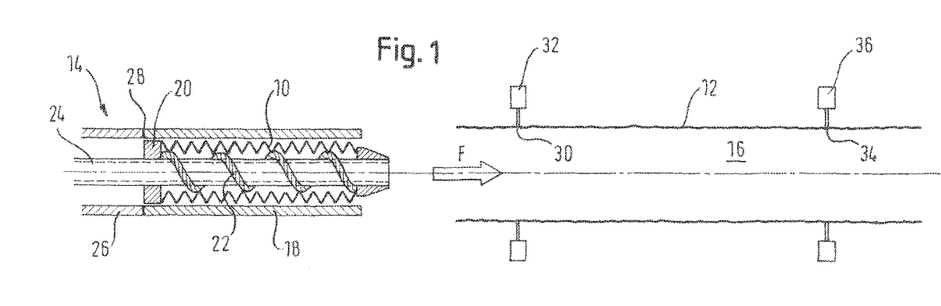
FIG. 1 is a longitudinal axial section through a device for loading a stent into a delivery sheath.

FIG. 1 shows a crimped covered stent 10 ready for deploying from a loading sheath into a delivery sheath 12, by advancing the stent 10, in a loading tool 14 into the lumen 16 of the sheath 12, in the direction of arrow F.

The loading sheath is similar to a conventional stent deployment sheath, sized to be at least the length of the stent together with a further approximate 20% in length to provide a tolerant landing zone for the stent. It is conventionally of a braided polymer catheter material, as is generally known in the art of stent delivery systems.

The stent 10 is a radially self-expanding nickel titanium alloy stent covered in an ePTFE film. This covered stent is constrained by a loading sheath 18 in a radially compact disposition. The stent is installed in the loading sheath 18 by a "crimping" procedure known per se in which a jig (not shown) compresses the stent radially inwardly, down to its compact disposition, whereupon the stent 10 and the loading sheath 18 are moved relative to each other axially (usually by holding the sheath 18 stationary and translating the stent 10 into the lumen of the sheath 18).

In the present embodiment, before the stent is crimped, there is inserted in its lumen a shaft 24 carrying a sequence of rings standing proud of the cylindrical surface of the shaft, or a spiral thread 22 running along the shaft. The covered stent is crimped down onto the shaft, whereupon the shaft can push the stent along its axis, supporting the stent all the way along the length of the stent, within its lumen.

In accordance with the present invention, the stent 10 is then "deployed" into the lumen 16 of the delivery sheath 12. For that deployment, the confining sheath 18 is pulled proximally by a pulling tube 26 contiguous with the proximal end 28 of the loading sheath 18.

During this pulling, one restrains the shaft 24 from axial movement, which prevents the stent from moving axially with the retreating loading sheath 18, so that the sheath remains in the desired location, inside the delivery sheath 12.

The delivery sheath 12 is of rather thin-walled PET tubular material. It is gripped at its proximal end 30 by an annular gripper chuck 32 and gripped at its distal end 34 by a similar annular gripping chuck 36, so that the two chucks 32 and 36 hold the opposite ends 30 and 34 of the delivery sheath 12 at a desired distance apart, while the stent is deployed into the sheath lumen 16.

Figure 2:
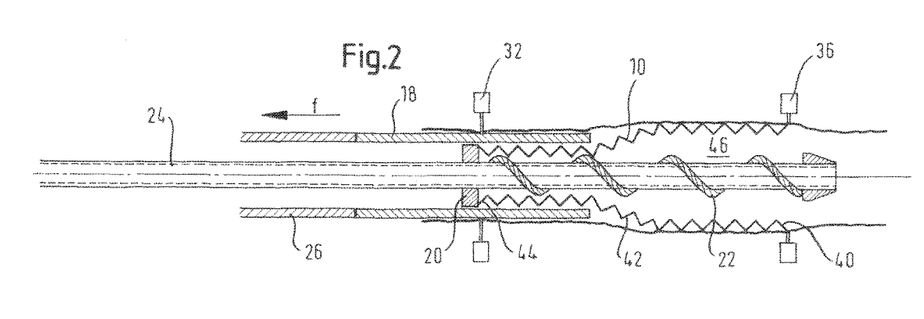
FIG. 2 shows the device of FIG. 1, but with the stent partially loaded in the sheath.

This deployment process can be seen, partially completed, in FIG. 2 of the drawings, where like reference numerals identify the same components as are shown in FIG. 1. It will be appreciated that the loading sheath 18 has moved proximally, in the direction of arrow f, relative to the stent and to the stent pusher annulus 20, thereby releasing the stent 10 into the lumen 16 of the delivery sheath 12 progressively, starting at the distal end 40 of the stent, through a radially expanding portion 42 of the stent that travels the full length of the stent, from the distal end 40 to the proximal end 44 of the stent, not yet free of the confining loading sheath 18 as shown in FIG. 2. Once the full length of the stent 10 is clear of the loading sheath 18, the full radially outwardly directed stenting force from the stent 10 is carried by the delivery sheath 12, and the lumen 46 of the stent is big enough for simple proximal withdrawal from that lumen of the tubular element 24 of the loading machine.

Figure 1A:
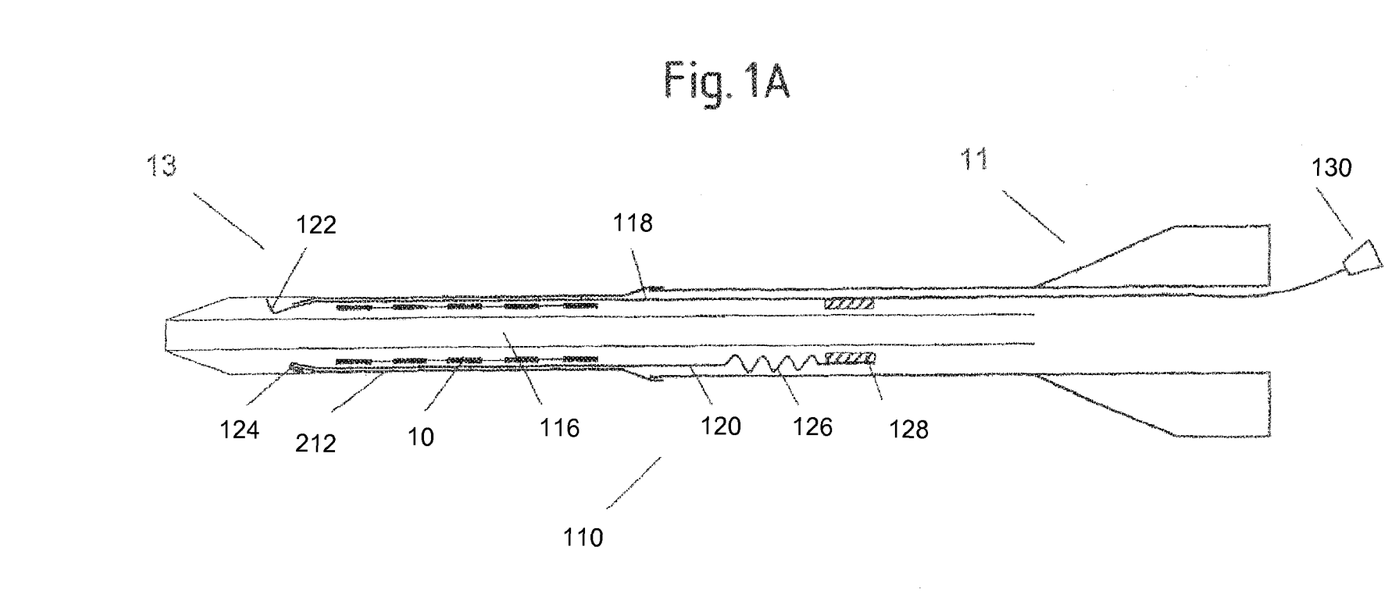
FIG. 1A shows an axial cross section of a stent delivery system in an initial position.

If it is needed to incorporate splitter wires, shown as 118, 20 in FIG. 1A, into the delivery system, they may be placed in the correct positions within the delivery sheath prior to deployment of the stent from the loading sheath into the delivery sheath. The stent may then be deployed against the splitter wires, to reach the desired configuration.

As explained above, the stent 10 is now radially confined within the delivery sheath 12 and can be regarded as a precursor for a "capsule" for placement at the distal end of a catheter delivery system for the stent. If desired, the loading sheath can be reused a number of times, for example ten times, before it is replaced.

Figure 3:
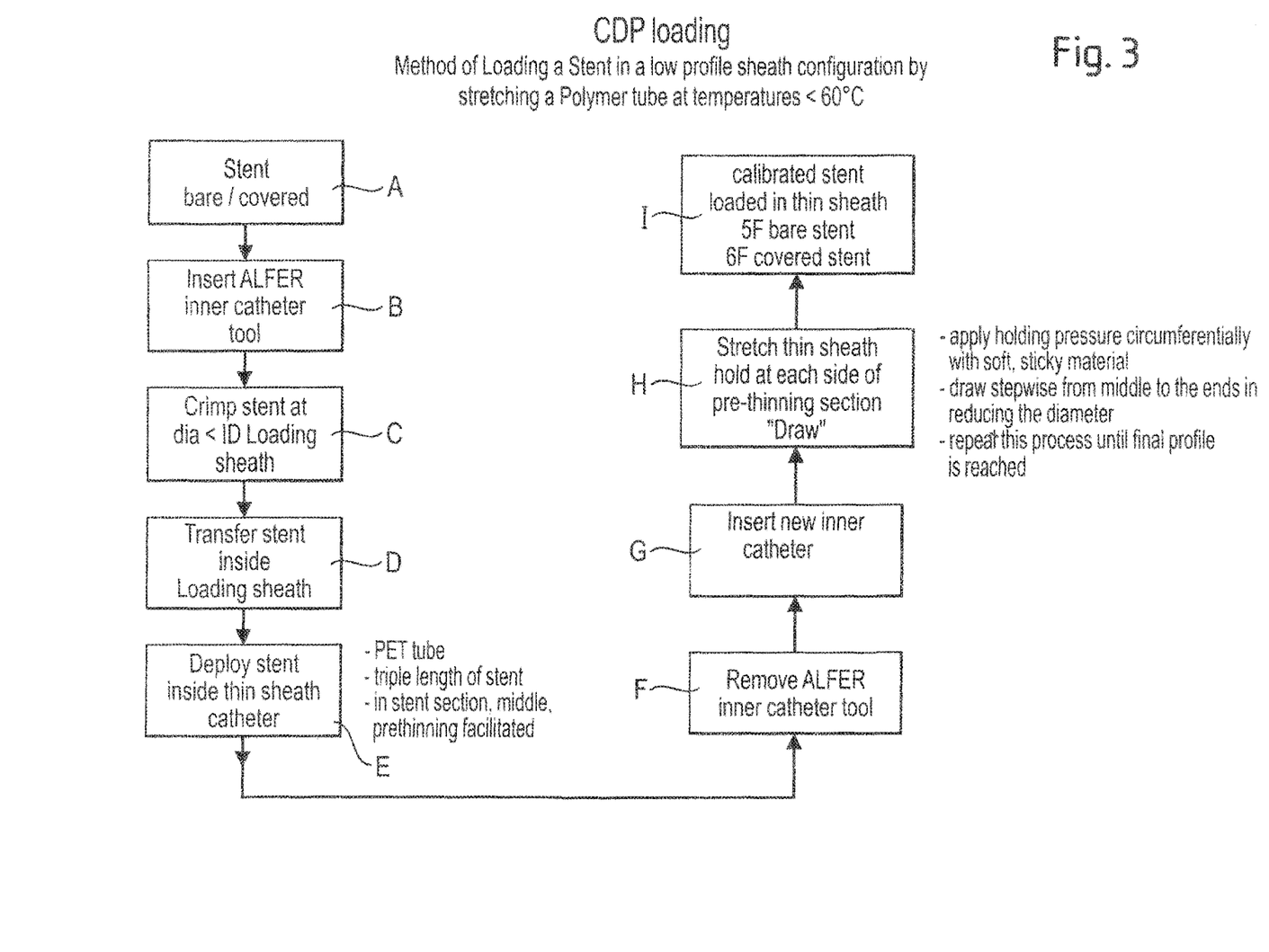
FIG. 3 is a flow diagram of method steps for installing a stent or stent graft within a sheath, in accordance with the present invention.
Figure 3A:
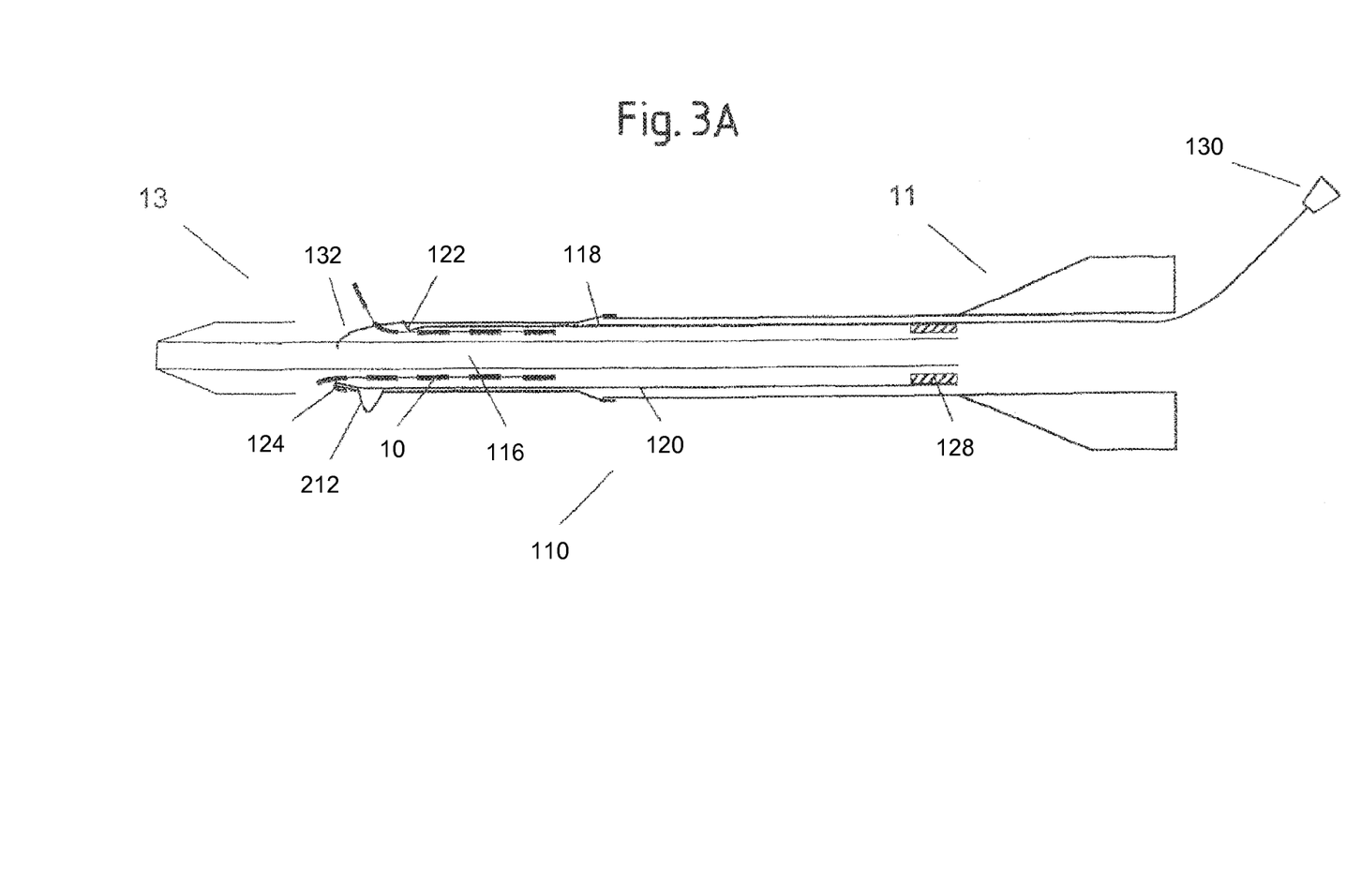
FIG. 3A shows an axial cross section of a stent delivery system in a second intermediate position, where the sheath removal process has started.

The process is presented in a block diagram, in drawing FIG. 3. However, FIG. 3 identifies further steps of the manufacturing process. The sequence of steps in FIG. 3 is identified by references A to I and we have the following comments on these process steps.

Step A is the step of providing the stent or stent graft of choice. A bare stent is one without any covering. A stent graft is a covered bare stent and the covering is typically of expanded polytetrafluoroethylene (ePTFE) but other covering materials are known to those skilled in the art.

Step B is the step of installing in the lumen of the chosen stent an inner catheter tool and the one preferred by the present Applicant is that described in its earlier publication WO 2004/096091 which goes by the acronym "ALFER".

Step C is the step of crimping the stent to bring the outside diameter of the chosen stent down to one that is small enough for loading the crimped stent into the chosen loading sheath 18. Next, step D, the crimped stent is translated axially into the lumen of the loading sheath 18. Then, the loading sheath carrying the stent is translated (as explained in FIGS. 1 and 2) into the lumen 16 of the delivery sheath 12 and the loading sheath 18 is withdrawn in order to deploy the stent into the delivery sheath. As noted on FIG. 3, the delivery sheath 12 is conveniently a PET tube having a length about three times that of the stent, with a pre-thinned zone in the PET tube located midway along the length of the stent in the lumen of the PET tube.

Once the stent is deployed, the inner catheter loading tool can be removed, step F, from the lumen of the deployed stent. At this point, step G, any desired component of the catheter delivery system which is to be located in the lumen of the stent can now be introduced into that lumen.

Of course, other methods of deploying stents into the lumens of e.g. body passages are known by those skilled in the art, and may with appropriate modification be employed to deploy the stent from the loading sheath to the delivery sheath in an equivalent manner.

Having prepared the stent lumen, the delivery sheath can now be cold-drawn, lengthwise, to impose substantial strain on the material of the delivery sheath. This strain will have the effect of reducing the wall thickness of the delivery sheath, and generating hoop stresses within the delivery sheath being cold-drawn, which hoop stresses will tend to compress the stent inside the lumen of the delivery sheath, and therefore marginally reduce its diameter. The FIG. block diagram carries notes in relation to this step H of the process. These notes teach to use a soft sticky material to grip the delivery sheath for achieving the cold-drawing strain. Such soft, sticky materials could be silicone rubber or an adhesive composition, for example. That strain is conveniently imposed on the sheath stepwise, commencing at the midpoint of the length of the sheath and repeating the cold-drawing process, stepwise, until a final desired outside diameter profile is achieved for the sheathed stent. For example, using two gripping chucks 32 and 36, the sheath is firstly gripped at each end by the two chucks. The chucks are drawn apart to create a weak zone at the middle of the sheath. Then, the sheath is simultaneously gripped in the middle by the first gripping chuck and at one end by the second gripping chuck, then the gripping chucks are slowly drawn apart. The second gripping chuck is now moved to the new middle of the drawn sheath, and the first gripping chuck to the other end. The gripping chucks are again drawn apart. This process is repeated until a desired delivery sheath diameter is reached.

Thus, in the final step I of the process, the stent-bearing capsule is ready for combining with other components of the catheter system that is to deliver the stent to the site of stenting in the body of a patient. This is done in an entirely conventional manner, for example heat-melting the inner catheter 24 with a member of the same diameter in the proximally proximate component of the delivery system.

There now follows an enabling description as to two ways to provide a splitting system for the sheath delivery catheter system described above.

Figure 2A:
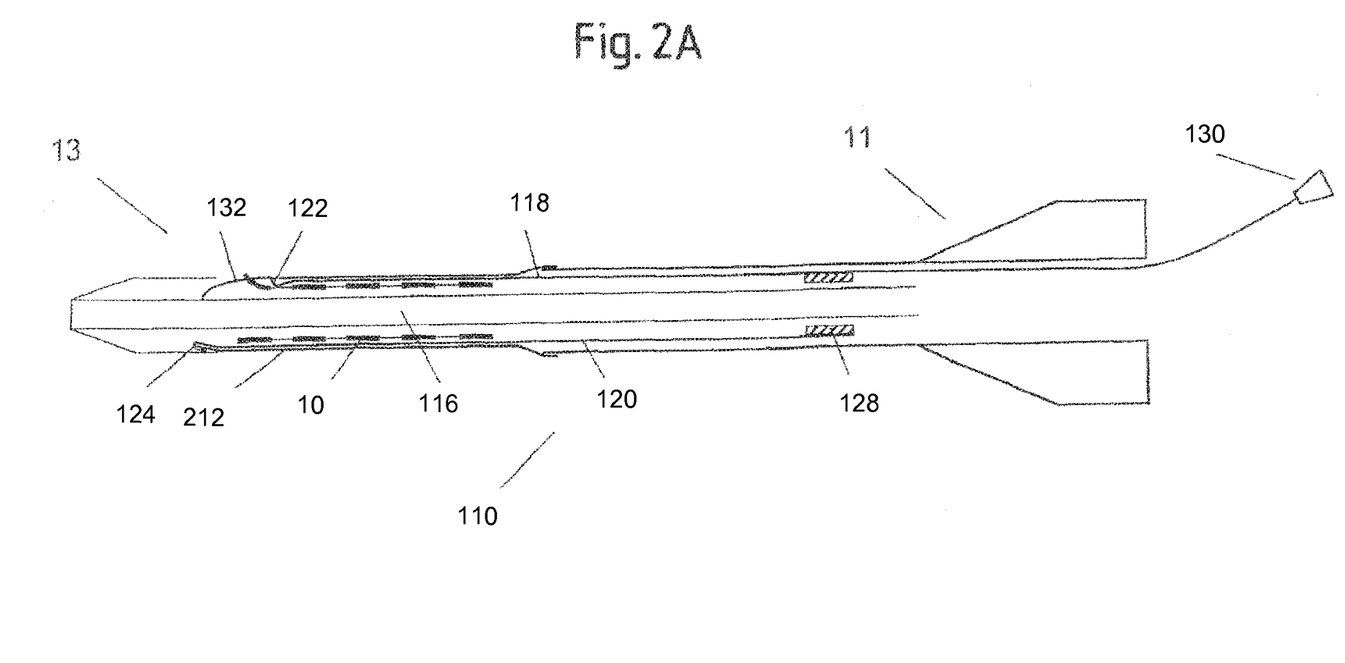
FIG. 2A shows an axial cross section of a stent delivery system in a first intermediate position, where the sheath cutting process has started.

A first way to provide a splitting system for the sheath delivery catheter system described above is described first. The reference numerals hereinbelow refer to the FIGS. 1A to 3A. FIG. 1A shows an axial cross section of a catheter delivery system 110 according in an initial position before expansion of the endoprosthesis. The delivery system 110 has a proximal end 11 and a distal end 13, comprising an elongate region 116 where a vascular self-expansible stent 10 is received. The stent 10 is surrounded and held in its radially compressed state by a sheath 114 made of PET. Further, the delivery system 110 comprises a first 118 and a second 120 pull element that both consist of a metallic wire and run between the stent 10 and the sheath 114 in the region 116 where the stent 10 is received. In this region 116, the wires of both pull elements 118, 120 are flattened along a circumferential direction of the stent 10, so as to have a ribbon-like shape. The first pull element 118 has a splitting section 122 at its distal end that is formed by a wire portion standing up in a radial direction of the delivery system 110 and a handle 130 attached to its proximal end for pulling the pull element 118 in a direction towards the proximal end 11 of the delivery system 110. The second pull element 120 has a hooked portion 124 at its distal end that is clamped onto the distal end of the sheath 114, so as to provide a secure attachment. At its distal end, the second pull element 120 is attached to a metallic ring 128 that is itself attached to the first pull element 118 and serves as a coupling mechanism. The two pull elements 118, 120 are arranged opposite each other on the circumference of the stent 10 and secured in this configuration by the coupling mechanism 128. Close to the coupling mechanism 128, the second pull element 120 has an undulating portion 126. For stent 10 deployment, the first pull element 118 is pulled towards the proximal end 11 of the delivery system 110, using the handle 130. This causes the splitting section 122 to move along the length of the stent 10 in the same direction, thereby splitting the sheath 114 along its length as is shown in FIG. 2A. In the section 132 of the distal catheter region 116, where the sheath 114 has already been split, the stent 10 starts to expand radially. Simultaneously the coupling mechanism 128 is moved towards the proximal end 11 of the delivery system by the first pull element 118, thereby pulling the distal end of the second pull element 120 in the same direction. FIG. 2A shows an axial cross section of the catheter delivery system 110 of FIG. 1A in a first intermediate position, where the second pull element 120 has been fully straightened and the undulating portion 126 has disappeared. However, the hooked portion 124 of the second pull element 120 is still in its initial position. Thus, the sheath 114 has been partially split and the stent 10 has started expanding in the split region 132, but the sheath 114 removal process has not started yet. When the first pull element 118 is pulled further towards the proximal delivery system end 11, the hooked portion 124 starts pulling the sheath 114 proximally from its distal end as can be seen in FIG. 3, showing the catheter delivery system 110 of FIGS. 1 and 2 in a second intermediate position. Once the sheath 114 is split along its whole length, the stent 10 fully expands into its radially expanded state. Subsequently, the sheath 114 is completely removed from the region 116 where the stent 10 is received, by further pulling the first pull element 118. Then the catheter delivery system 110, including the split sheath 114, can be taken out of the patient's body.

This represents an example for a combination of the two aspects of the invention and illustrates the advantages of such a configuration: sheath splitting and removal can be performed reliably and quickly in one work step, simply by pulling a single pull element 118; the danger of damage to body tissue due to moving elements is minimised; entanglement of different pull elements is avoided; and the distal end profile of the catheter delivery system 110 can be reduced, allowing accurate placement and controlled deployment even of very small endoprostheses.

There is now described a second way of providing a splitting system for the sheath delivery catheter system described above. The reference numerals hereinbelow refer to the FIGS. 4A to 7A. Referring first to drawing FIG. 4A, a self-expanding nickel-titanium shape memory alloy stent 10 is confined within a sheath 212 in a catheter device 214 which constitutes a transluminal delivery system for the stent 10, that has a tapered atraumatic distal tip 216. The catheter has a shaft 218 that defines a bore 220 for a guidewire along which the catheter delivery system may be advanced until its distal end zone carrying the zone is in the desired site of stenting.

Figure 4A:
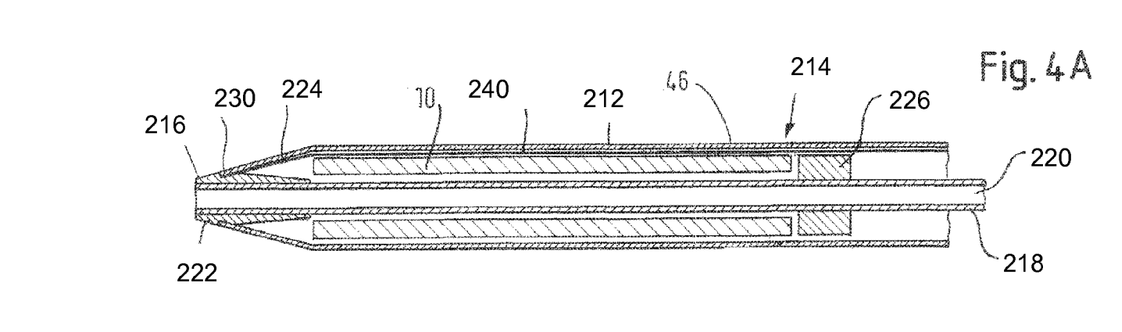
FIG. 4A is a diametric longitudinal section through the distal end of a stent delivery system.
Figure 5A:
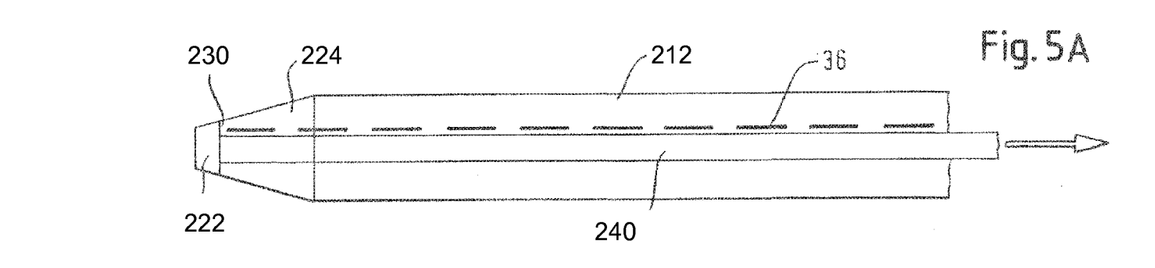
FIG. 5A is a section that is the same as FIG. 4A, but shows only the sheath and elongate pull element of FIG. 4A, for improved clarity.

Carried on the shaft 218 at its distal end zone is a distal tip element 222 that receives an inwardly tapered end portion 224 of the sheath 212 surrounding the stent. At the proximal end of the stent 10 is a pusher annulus 226 that is also a radiopaque marker and is fixed to the outside surface of the catheter shaft element 218. When the time comes to deploy the self-expanding stent 10, the hoop stresses in the sheath 212 surrounding the stent 10 have to be released, so that the stent 10 can expand radially into the stenting site within the bodily lumen. Conventionally, this is accomplished by simply pulling the sheath 212 proximally until it slides over the stent 10, withdrawing proximally relative to the stent, to release the stent progressively, starting at its distal end, into the bodily lumen. However, with the present invention, the stent release mechanism is quite different, as will now be explained with reference to FIGS. 5A and 6A of the drawings.

Figure 6A:
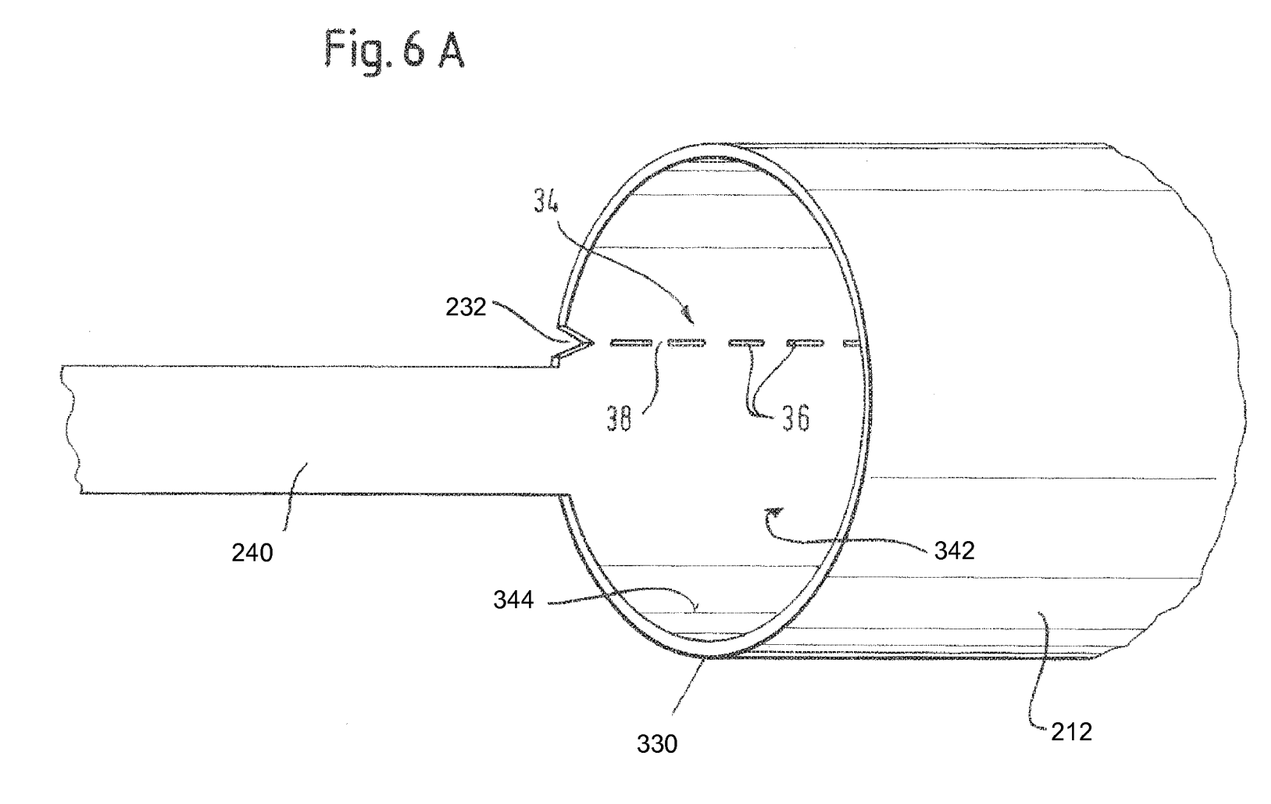
FIG. 6A is a view from the side, of the distal end of the sheath and pull element of FIG. 5A.

First looking at FIG. 6A, we see distal end 230 of the sheath 212, with a circumference that includes a short slit or "nick" that will serve as a tearing initiation point on the circumference of the distal end 230. Extending proximally from the tearing initiation site 232 is a line of weakness 34 that is created by a line of elongate perforations 36, co-linear and spaced from each other to provide a line of weakness running all the way from the tearing initiation site 232 to the proximal end annulus of the sheath 212. The residual material 38 in the gaps between the slits 36 is sufficient to maintain the hoop stresses and integrity of the sheath 212 until the moment when it is desired to release the stent by tearing down the line of weakness by rupturing the sequence of material bridges 38 between adjacent slits 36.

To accomplish this task, there is employed a pull element 240 which is shown in FIG. 6A extending distally away from the end annulus 330 of the sheath 212 but which is in actual use of the device folded inside the open end 342 of the sheath 212 so that it lies sandwiched between the stent 10 and the inside surface 344 of the sheath 212, running the full length of the stent 10 and extending further, proximally, beyond the pusher annulus 226. Not visible in the drawings, but nevertheless indicated by reference 46, is a coating of hydrophilic material on the major surfaces of the sheath 212. Not shown in the drawings (but those skilled in the art will be able to develop the details for themselves) is the structure of the catheter proximal of the pushing annulus 226. The catheter shaft might be of the "over the wire" variety or of the "rapid exchange" variety, depending on the length of the guidewire lumen. There needs to be in the shaft a pushing member (conveniently a tube) to convey the endwise compressive stress to the pusher 226. Further, there needs to be a pull element (conveniently a pull wire) to deliver to the pull element 240 the necessary tensile stress to tear the sheath. Conveniently, the connection between the pull wire running the length of the catheter shaft, and the pull element 240 that extends from proximal of the pusher annulus 226 to the distal end of the sheath 212, is an annular element that slides on the shaft 218 and conveniently serves as a radiopaque marker of the progress of the pulling element 240 as it progresses proximally release of the stent.

Alternatively, the pull element might extend proximally the full length of the catheter. Proximal of the stent, it could be twirled into a strand with a helical trace on its cylindrical surface, that extends along a pull wire lumen in the catheter shaft.

Figure 7A:
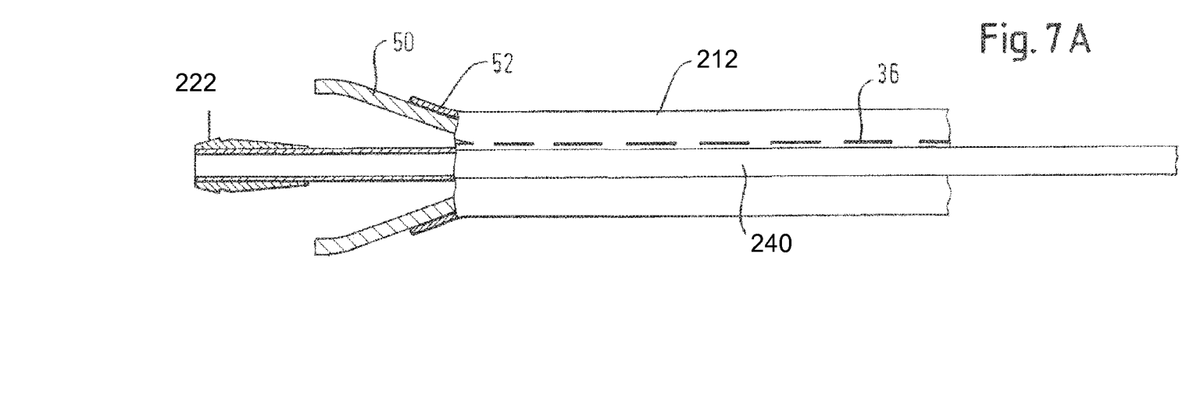
FIG. 7A is a section corresponding to that of FIG. 4A, but showing the system part way through the process of stent release.

Turning now to FIG. 7A, we can observe the stent release process with a "snapshot" of the process in progress, with a distal portion 50 of the stent 10 already released from the radially confining effect of the sheath 212, as the pull element 240 moves proximally relative to the stent 10 lying radially inside it and the sheath 212 laying radially outside it. This proximal progress of the pull element 240 draws into the annulus between the untorn sheath 212 and the stent 10 the distal-most portion of the sheath 212, that has already been parted along the line of weakness 34, thereby releasing hoop stresses in the distal-most portion of the sheath 212 and allowing it to relax distally outwardly, even as it finds itself being pulled proximally into the annulus between the untorn sheath 212 and the stent 10. This distal-most portion of the sheath is indicated by reference 52 in FIG. 7A. We can already see in FIG. 7A that the sheath no longer extends all the way to the distal end of the stent 10, precisely because the proximal movement of the pull element 240 causes the sheath to double back on itself, radially inwardly. It should be remembered that the inherent stiffness of the sheath is remarkably low, because the PET material of which the sheath is formed has a high modulus of elasticity and high physical strength so that its wall thickness can be remarkably small. Once the hoop stresses in the distal-most portion of the sheath are relieved, this distal portion of the sheath is remarkably compliant and amenable to the creasing and folding that is going to occur when a full 360° circumference is pulled proximally by a pull element 240 that extends around only a portion of that circumference adjacent to the line of weakness where the sheath is progressively rupturing from its distal end to its proximal end.

By the time the tearing of the sheath has progressed as far as the proximal end of the stent, the entire length of the stent will have expanded radially into position in the bodily lumen to be stented, and any portion of the sheath 212 that lies sandwiched between the stent and the bodily lumen will be only at the zone of the stent closest to its proximal end and will therefore be relatively easily withdrawn from between the stent and the bodily lumen, as soon as the stent delivery system as a whole is pulled proximally away from the deployed stent.

It will apparent, then, to readers skilled in this art that the architecture of the distal end of the stent delivery system offers possibilities to get the passing diameter of that distal end zone down to values hitherto not obtained, because the sheath can be made of ultra-thin material. Furthermore, it is possible to contemplate deployment of extremely long stents, simply because the sheath is being steadily withdrawn proximally from its location between the expanding stent and the tissue of the bodily lumen, all the while that the sheath is being progressively torn along the line of weakness from its distal end to its proximal end, leaving sandwiched between the stent and the bodily lumen, when stent deployment is complete, a much smaller amount of sheath material than would be the case with for example a sheath slitting "cheesewire" as in EP-A-732087 or WO 2001/008599, each of which is incorporated by reference into this application, that slit the sheath but do not withdraw it proximally during the stent deployment period.

Other variations will be evident to those skilled in the art. Specifically, the idea of providing a pull element between two parallel lines of weakness, so that the arc of sheath material between the two lines of weakness is pulled proximally by the pull element, but not the arc on the other side of the diameter of the sheath, is an intermediate example between the previously proposed "cheesewire" system in which the full circumference of the sheath continues to lie between the expanded stent and the wall of the bodily lumen, and the "single line of weakness" example shown in the present drawings, in which the full circumference of the sheath is pulled proximally with the pull element 240. Suppose, for example, that the pull element 240 is a band that extends around a substantial part of the circumference of the sheath, for example, halfway around the circumference of the sheath. In such a case, proximal withdrawal of half the sheath material will leave for withdrawal after stent deployment sheath material amounting to only half of the circumference, instead of the prior art full circumference. This is worthwhile progress, especially with lengthy devices to be placed in the lumen.

Although the presently preferred material for the sheath is PET, this does not exclude other materials. Materials selection is part of the routine duties of the person skilled in the art when seeking to optimise stent delivery systems. For the present inventors, as of now, the "best mode" involves using a sheath of PET, cold drawn (that is to say, drawn at a temperature of 50° C. or less) and with a wall thickness after cold drawing (and with the stent or stent graft inside the PET tube lumen) of 0.035 mm (or even less). With the pull element serving to drag material of the sheath into the annulus between the stent and the untorn sheath, it will generally be beneficial to provide the sheath material with a hydrophilic coating which will attract water molecules to the coating to serve as a lubricant, even while the pull element pulls the torn sheath proximally over the stent until the stent is fully released. Advantageously, the distal tip of the sheath is drawn down to an outside diameter that is substantially smaller than the outside diameter of the sheath where it embraces the self-expanding device, in order that the sheath shall itself define the outside of an atraumatic tip section for the delivery system as such.

Readers will understand that the illustrated embodiments are non-limiting. Readers have enough background technical knowledge to modify the specific teachings above so as to conform to their own perceptions of good design and conformity with their own stent products or other requirements of the market. Those skilled in the art will build on their specialist background knowledge when considering the above disclosures, factoring into their consideration of the present disclosure the specialist knowledge that they have from their own experience in this field. Quite evidently, engineers from other corporations will have their own design history and preferred ways of implementing the teachings set out above. The claims that follow seek to define the present inventive concept and should not be seen as directed exclusively to the illustrated embodiments, nor should they be seen as limited to mechanical equivalents of features shown in the illustrated embodiments. All publications and patent applications cited in this specification are herein incorporated by reference in their entirety as if each individual publication or patent application were specifically and individually put forth herein.

What is claimed is:

1. A method of loading a self-expanding stent into a delivery sheath comprising the steps of:
   radially compressing the stent from an outside diameter $d0$ to an outside diameter $d1$;
   providing a loading sheath having an inner diameter $d2$, where $d0 > d2 > d1$;
   after the providing a loading sheath step
   inserting the compressed stent into a loading sheath lumen;
   providing a delivery sheath having an inner diameter $d3$, where $d0 > d3 > d2$, wherein the delivery sheath is gripped at its opposing ends by first and second sheath grippers; then
   inserting the loading sheath, containing the stent, into a delivery sheath lumen;
   deploying the stent into the delivery sheath lumen; and
   decreasing the delivery sheath inner diameter to a diameter $d4$ which is less than $d3$ by longitudinally stretching the delivery sheath with the first and second sheath grippers.

2. The method according to claim 1 wherein deploying the stent into the delivery sheath lumen includes sliding the loading sheath out of the delivery sheath while restraining the stent from moving out of the delivery sheath.

3. The method according to claim 1 further comprising deploying the stent located in the delivery sheath by causing the delivery sheath to part along a line axially extending the length of the stent.

4. The method according to claim 1 wherein the delivery sheath is made of polyethyleneterephthalate.

5. The method according to claim 1 wherein the delivery sheath has a wall thickness of approximately 20 µm before longitudinal stretching.

6. The method according to claim 1 wherein the delivery sheath exhibits a strain initiation zone from which a strain spreads out to facilitate the longitudinal stretching, progressively along the length of the delivery sheath.

7. The method according to claim 6 further comprising positioning the strain initiation zone between the opposing ends of the stent.

8. The method according to claim 7 further comprising locating the strain initiation zone mid-way between the stent ends.

9. The method according to claim 8 further comprising using a tool to insert the stent into the delivery sheath wherein the tool has a portion that extends along at least a part of the stent length.

10. The method according to claim 8 further comprising
- using a tool to insert the stent into the delivery sheath wherein the tool has a portion that extends along at least a part of the stent length
and
- removing the tool before longitudinally stretching the delivery sheath.

11. The method according to claim 10 further comprising introducing a stent delivery system component into the stent before longitudinally stretching the delivery sheath.

12. The method according to claim 11 further comprising providing a splitter disposed between the stent and the delivery sheath and that is adapted to split the delivery sheath when actuated.

13. The method according to claim 6 wherein the strain initiation zone comprises a portion of the delivery sheath that exhibits a reduced wall thickness.

14. The method according to claim 1 wherein longitudinally stretching the delivery sheath comprises providing a tool comprising the first and second sheath grippers.

15. The method according to claim 14 wherein the first and second sheath grippers grip around the delivery sheath circumference.

16. The method according to claim 15 in which at least one of the first and second sheath grippers comprises a high friction grip surface comprising silicone rubber material to contact the delivery sheath.

17. The method according to claim 1 in which the longitudinally stretched delivery sheath exhibits an outside diameter of not more than 6 French (2 mm).

18. The method according to claim 1 wherein a shaft is inserted into a lumen of the stent before the stent is radially compressed and the shaft comprises a spiral along a length of the shaft.

* * * * *